United States Patent [19]

Bonacker et al.

[11] 4,118,349

[45] Oct. 3, 1978

[54] PROCESS FOR THE MANUFACTURE OF POLYSTYRENE LATEX COMPOUNDS

[75] Inventors: Ludwig Bonacker, Marbach near Marburg, Lahn; Josef Stark, Marburg, Lahn, both of Fed. Rep. of Germany

[73] Assignee: Behringwerke Aktiengesellschaft, Marburg, Lahn, Fed. Rep. of Germany

[21] Appl. No.: 811,853

[22] Filed: Jun. 30, 1977

Related U.S. Application Data

[63] Continuation of Ser. No. 546,904, Feb. 4, 1975, abandoned, which is a continuation-in-part of Ser. No. 252,028, May 10, 1972, abandoned.

[30] Foreign Application Priority Data

May 12, 1971 [DE] Fed. Rep. of Germany ......... 212348

[51] Int. Cl.$^2$ ............................................. C08L 89/00
[52] U.S. Cl. .................................. 260/8; 260/112 R; 260/121; 195/63; 195/68; 424/9; 424/12
[58] Field of Search ................. 260/8, 112 R; 424/12, 424/9

[56] References Cited

U.S. PATENT DOCUMENTS

| | | | |
|---|---|---|---|
| 3,088,875 | 5/1963 | Fisk | 424/12 |
| 3,234,096 | 2/1966 | Pollack | 424/9 |
| 3,236,732 | 2/1966 | Arquilla | 424/12 X |
| 3,313,749 | 4/1967 | Ready | 260/8 |
| 3,442,826 | 5/1969 | Dekking | 260/8 |
| 3,551,555 | 12/1970 | Schuurs | 424/12 |
| 3,574,062 | 4/1971 | Sato | 260/121 |
| 3,639,558 | 2/1972 | Csizma | 424/12 |
| 3,843,447 | 10/1974 | Burkoth | 260/112 R |
| 3,857,931 | 12/1974 | Hager | 424/12 |

FOREIGN PATENT DOCUMENTS

| | | | |
|---|---|---|---|
| 1,475,600 | 2/1967 | France | 424/12 |
| 993,961 | 6/1965 | United Kingdom | 260/8 |

*Primary Examiner*—Edward M. Woodberry
*Attorney, Agent, or Firm*—Curtis, Morris & Safford

[57] ABSTRACT

The present invention relates to a process for the manufacture of protein or peptide polystyrene latex compounds useful as diagnostic agents, in which a protein or peptide is linked by means of an aromatic diazonium compound to a homo- or copolymer of styrene as well as the compounds obtained by said process.

22 Claims, No Drawings

PROCESS FOR THE MANUFACTURE OF POLYSTYRENE LATEX COMPOUNDS

This application is a continuation of application Ser. No. 546,904 filed Feb. 4, 1975 and now abandoned, which in turn is a continuation-in-part of application Ser. No. 252,028 filed May 10, 1972 and also now abandoned.

The present invention relates to novel protein- or peptide- polystyrene latex compounds which are used as diagnostic agents, and to a process for their manufacture.

The known diagnostic agents made from polystyrene and proteins consist of an aqueous suspension containing polystyrene particles to which proteins or peptides are linked by adsorption and, optionally a buffer system. When a protein or peptide so adsorbed reacts with its corresponding antibody, the polystyrene precipitates in fine flakes. In this manner, the positive reaction between antigen and antibody can be made visible.

However, the diagnostic agents obtained by adsorption of a protein to polystyrene latex have the disadvantage of a limited stability, since the adsorption reaction is reversible and therefore results in a desorption reaction in many cases.

With some proteins, it has hitherto not at all been possible to link them to polystyrene latex by adsorption. Such proteins could therefore not be used to obtain diagnostic agents by means of polystyrene latex.

A protein- or peptide- polystyrene latex compound of the invention comprises a protein or peptide which is linked to polystyrene by means of an aromatic diazonium compound.

Accordingly, the process of the invention comprises reacting a polystyrene latex suspension, a protein or peptide and an aromatic diazonium compound with each other under conditions which allow the formation of a compound being useful as a diagnostic agent.

According to the process of the invention, immunologically active proteins or peptides, which are available trade products or can be prepared in known manner, for example plasma proteins, such as albumin, alpha-globulin, beta-globulin, gamma-globulin, thrombin, plasmin; proteohormones, such as the peptide insulin and the protein chloriogonadotropin; proteins obtained from viruses, such as rubella virus; from bacteria, such as alphahemolysin obtained from staphylococci; from protozoae, such as Trypanosoma cruzi and entameba histolytica; from helminthes, such as Schistosoma mansoni, can be linked to polystyrene latex.

Suitable aromatic diazonium compounds according to the invention are diazotized aromatic amines, preferably amines containing one or several further functional groups, such as sulfonic acid or diazo groups, for example the diazotization products of 2-naphthylamine, 7-ethoxy-3,9-diamino-acridine, aniline, substituted anilines, such as 2,5-dichloro-4-nitro-aniline, phenylene diamine, benzidine, dianisidine, diamino-diphenylmethane, diamino-diphenyl-sulfone, benzidine-sulfonic acid and p-amino-phenylsulfone-ethoxy-sulfonic acid of the formula

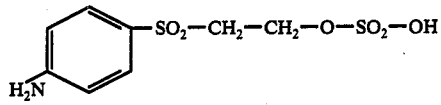

As polystyrene latices there are suitable not only those obtained from homopolymers of styrene but also from copolymers containing more than half the molecular weight of styrene monomer units, namely copolymers of styrene with acrylic or methacrylic acid. To ensure good properties of the product the particle size of the latices has to be between 0.1 and 1 micrometers ($10^{-6}$ meters), preferably between 0.2 and 0.3 micrometers. Suitable latices are, for example, the following: polystyrene latex 24016, lytron 602 and lytron 615, manufactured by British drug houses; latex calibers, 0,8 μm, latex calibers 0,25 μm, rhodopas sb 030, rhodopas sd 101, manufactured by Phone-Progil, hycar latex 1512 and hycar latex 2600 × 120, manufactured by Hycar and amsco res 4150 and amsco res 3011, manufactured by Amsco.

In order to establish whether a specific polystyrene latex will give satisfactory results in the present process, a small amount thereof can be reacted as a test batch in the manner described.

To stabilize the suspension and to make it suitable for the intended purpose it is essential to add, as a stabilizer, albumin, preferably serum albumin and more preferably human serum albumin in an amount of 0.5 to 1.5% calculated on the finished product. Further stabilizers, for example glycerol, may also be added to the composition obtained according to the invention. Moreover, the suspension may be homogenized by shaking, stirring or treating it by ultrasound. It is essential that the latex is kept in a homogenous phase during the whole process. Homogenous in this sense means that the latex particles are equally distributed in the aqueous liquid carrier in such a manner that each volume unit of the latex contains about the same number of solid particles. In addition it is advantageous to use Latices, the particles of which are of about equal size, i.e., such which have a narrow range of size distribution.

According to the invention, it is advantageous first to dilute a polystyrene latex suspension to a solid content of about 5 to 15% by weight, preferably of 10% by weight.

An addition of a stabilizer, for example glycerol, in an amount of about 2% by volume has proved suitable in many cases.

To this mixture, either the diazonium salt solution prepared in a separate vessel is added or the amino compound used as a starting substance for this purpose is introduced as such and the mixture is diazotized in known manner in the presence of the other reaction components. The admixing of the components and the diazotation reaction have to be carried out at a temperature below room temperature, preferably in the range between 2° and 8° C.

In some cases, especially when p-amino-phenylsulfone-ethoxysulfonic acid is used, this compound may also be added as a solid substance to the polystyrene latex suspension. In this case, it is advisable to stir the suspension for 10 to 20 hours, preferably for 15 hours, at a temperature of 30° to 80° C., preferably of 40° C., and to remove excess p-aminophenyl-sulfone-ethoxy-sulfonic acid prior to further processing. The amino group is then diazotized in known manner at the low temperature mentioned above, i.e., in the range between 2° and 8° C.

The end of the diazotation reaction, which is generally reached after 15 minutes, can be verified in known manner, for example by means of β-naphthol in dilute sodium hydroxide solution. The polystyrene latex particles then take a pink to red color.

If this reaction is positive, the immunologically active peptide or protein is added, while cooling, for example at 2°–8° C., preferably at 4° C., in a weakly alkaline solution, for example at pH 7.5–9.5, preferably at pH 8.5, to the polystyrene coupling product. To adjust a weakly alkaline pH, buffer mixtures, especially containing boric acid, are suitable.

According to another embodiment of the invention the protein or peptide, suitably dissolved in a buffer solution, is added to the polystyrene latex, the whole is kept at a weakly alkaline pH preferably between 7.5 and 9.5 and at a temperature below room temperature preferably 2°–8° C., and the diazonium solution prepared in a separate vessel is added.

After about 2 hours albumin, preferably a 20% human serum albumin solution, is added in an amount to give a content of 0.5 to 1.5% in the final product. The product may be homogenized, e.g., by a treatment with ultrasound. If the composition prepared according to the invention is to be diluted, at the same time, to a determined concentration, a 0.5 to 1.5% human serum albumin solution is advantageously used for this purpose.

The irreversible linkage of the protein or peptide to the polystyrene particles in the reagents of the invention is evidenced by the following test:

TEST 2 ml of a commercial 40% polystyrene latex suspension (see Example 1) were diluted with 5 ml of a 0.2-molar borate buffer of pH 8.5, containing 2% by volume of glycerol as a stabilizer. Subsequently, 40 mg of gamma-globulin taken from rabbits, that contained an antibody specificity against hepatitis-associated antigen (HAA) and which had been dissolved in 1 ml of a 0.2-molar borate buffer of pH 8.5, were added. The suspension was cooled, while stirring, to +4° C. 0.08 ml of a 0.2% solution of bis-diazotized benzidine (prepared as in Example 3) was then added. After 1 hour, the reaction mixture was diluted with 0.2-molar borate buffer of pH 8.5 to a volume of 30 ml.

The reaction mixture was then divided into 4 equal volumes of 7.5 ml each. The 4 portions were centrifuged for 1 hour at 40,000 g.

In the supernatant substances, no protein could be established by precipitation with 1.0 ml of 50% trichloroacetic acid per 5 ml of supernatant substance. For comparison's sake, a solution of 6.67 mg of the gamma-globulin taken from rabbits were reacted at +4° C. with 0.013 ml of 0.2% bis-diazotized benzidine in 5 ml of 0.2-molar borate buffer of pH 8.5, and 1.0 ml of 50% trichloroacetic acid was added. The precipitate was centrifuged, dissolved in 5 ml of 0.1-molar sodium hydroxide and used for a nitrogen analysis. In the comparative sample, 0.2 mg of nitrogen/ml was determined, whereas there was no precipitate obtained with trichloroacetic acid in the supernatant substances of the four portions, nor was nitrogen found. This shows that all protein is bound to the polystyrene particles.

The sediments of the four portions were again suspended twice with 5 ml each of the following solutions and centrifuged at 40,000 g for 1 hour.
1. 5% by volume of dimethyl sulfoxide in water
2. 5 mols/l of urea in water
3. 1 mol/l of sodium chloride in 0.2-molar borate buffer of pH 8.5.
4. 1 mol/l of sodium chloride in 0.2-molar sodium acetate buffer of pH 5.0.

By the indicated treatment, 2 supernatant solutions each were obtained from the four sediments, that is a total of 8 supernatant solutions, which were dialyzed against 0.2-molar borate buffer of pH 8.5 and then concentrated to a volume of 5 ml by means of a collodion bag apparatus (manufactured by Messrs. Sartorius Membranfiltergesellschaft, Gottingen, W-Germany). In none of the 8 supernatant solutions was a precipitate obtained with 1 ml of 50% trichloroactic acid. Hence, no protein was desorbed from the polystyrene latex.

After the second centrifuging operation, the residues were again suspended each with a 1.5% human albumin solution in 0.2-molar borate buffer of pH 8.5 and the suspensions were homogenized by a 30-second ultrasonic treatment at 20 kc/s. and 125 watt.

The four suspensions react with sera containing HAA, while forming an agglutination.

The test demonstrates that, in spite of stringent conditions, no immunologically active material was split off from the polystyrene latex particles and that the activity of these particles is fully preserved despite this treatment.

The following Examples serve to illustrate the invention

EXAMPLE 1

10 ml of a commercial 40% polystyrene latex suspension (Polystyrene Latex manufactured by The British Drug Houses Ltd) were diluted, while stirring, with 40 ml of 0.2-molar sodium hydroxide solution. 200 mg of p-aminophenyl-sulfone-ethoxy-sulfonic acid were added to this suspension. The mixture was stirred for 3 hours at 40° C. and then dialyzed for 15 hours at 20° C. against distilled water. After dialysis, the suspension was cooled to 4° C. and 15 ml of 0.15-molar hydrochloric acid and 4 ml of a 0.2-molar sodium nitrite solution were added, while stirring.

When the reaction with beta-naphthol was positive, the immunologically active peptide or protein to be linked to the polystyrene latex, which active material had been dissolved in 100 ml of a 0.2-molar boric acid-borax buffer solution, hereinafter referred to as borate buffer of pH 8.5, and cooled to 4° C., was added to the coupling product. The following immunologically active peptides and proteins were used for carrying out the process of the invention according to Example 1:
 (a) 50 mg of human choriogonadotropin (HCG), 3220 U/mg,
 (b) 50 mg of crystallized zinc insulin taken from cattle,
 (c) 50 mg of crystallized zinc insulin taken from pigs,
 (d) 200 mg of anti-immunoglobulin M taken from rabbits or
 (e) 200 mg of anti-HAA gamma-globulin taken from rabbits.

Two hours after the addition of the solution of the immunologically active peptide or protein, 7.5 ml of a 20% aqueous human serum albumin solution were added to the mixtures with human choriogonadotropin (a) and to the mixtures with zinc insulin taken from cattle and pigs (b) and (c), whereby concentrations of about 0.5% of human serum albumin in the final product results, and 15 ml of a 20% human serum albumin solution were added to the mixtures with the two gamma-globulins (d) and (e), whereby a concentration of about 1% of human serum albumin in the final product results. Each of the five mixtures described was diluted with 0.2-molar borate buffer of pH 8.5 to a volume of 300 ml and homogenized in a continuous flow by means of ultrasound of a frequency of 20 k.c./s. At an ultrasonic power of 750 watt the mixtures of 300 ml could be homogenized within 15 minutes.

EXAMPLE 2

10 ml of the 40% polystyrene latex suspension as detailed in Example 1 were diluted while stirring with a solution of 50 mg of 7-ethoxy-3,9-diamino-acridine lactate in 30 ml of water. After stirring had been continued for 1 hour, 10 ml of 1N sulfuric acid were added. The mixture was then cooled to +4° C. and 5 ml of 0.2-molar sodium nitrite were added. After stirring had been continued for another 30 minutes at 4° C., the diazotized suspension was introduced while stirring into 200 ml of a solution of 0.1% anti-HAA-gamma globulin solution taken from rabbits, which solution had been previously cooled to 4° C., in 0.2-molar sodium borate buffer of pH 8.5, this pH-value being maintained at 8.5 during the introduction of the acid suspension by dropwise addition of 0.5N sodium hydroxide solution. The cooling bath was removed after 5 to 6 hours. After stirring had been continued for 15 hours at 20° C., 15 ml of a 20% human serum albumin solution were added and the mixture was diluted to a volume of 300 ml with 0.2-molar borate buffer of pH 8.5. The ultrasonic treatment was carried out as disclosed in Example 1.

EXAMPLE 3

10 ml of the 40% polystyrene latex suspension disclosed in detail in Example 1 were diluted to a volume of 60 ml with 0.2-molar borate buffer of pH 8.5, containing 2% by volume of glycerol as a stabilizer. The solution containing the immunologically active peptide or protein was added to this suspension. The mixture was cooled to 4° C., 0.4 ml of an aqueous solution of 0.2% by weight of bis-diazotized benzidine, which had been obtained from benzidine by a treatment with sodium nitrite in 0.2-molar hydrochloric acid at 4° C., was added and the whole was stirred at 4° C. for 1 hour. The mixture was then diluted to 300 ml with a 1% human serum albumin solution in borate buffer of pH 8.5. The following immunologically active peptides and proteins were used to carry out the process according to Example 3.

(a) 10 ml of a 2% anti-HAA gamma-globulin solution taken from rabbits,
(b) 100 mg of zinc insulin taken from pigs, dissolved in 60 ml of 0.2-molar borate buffer of pH 8.5,
(c) 100 mg of zinc insulin taken from cattle, dissolved in 60 ml of 0.2-molar borate buffer of pH 8.5,
(d) 10 ml of a 2% IgE solution or of a 2% anti-IgE gamma-globulin solution, taken from rabbits,
(e) 10 ml of a 2% anti-IgA gamma-globulin solution, taken from rabbits,
(f) 10 ml of a 2% anti-alpha$_1$-fetoprotein gamma-globulin solution taken from rabbits,
(g) 10 ml of a 2% solution of an anti-pregnancy protein (PP$_1$, PP$_2$ or PP$_3$) gamma-globulin, taken from rabbits,
(h) 10 ml of a 2% anti-human-placenta lactogen (HPL) gamma-globulin solution, taken from rabbits,
(i) 10 ml of a 2% anti-fibrinogen-split D gamma-globulin solution, taken from rabbits,
(j) 10 ml of a 2% anti-fibrinogen-split E gamma-globulin solution, taken from rabbits,
(k) 10 ml of a 2% anti-myoglobin gamma-globulin solution, taken from rabbits,
(l) 10 ml of a 2% anti-haptoglobin gamma-globulin solution, taken from rabbits,
(m) 10 ml of a 2% anti-C-reactive protein (CRP) gamma-globulin solution, taken from rabbits,
(n) 10 ml of a 2% anti-alpha$_1$-anti-trypsin gamma globulin solution, taken from rabbits, and
(o) 10 ml of a 2% anti-transaminase gamma-globulin solution, taken from rabbits.

In an analogous manner, the corresponding compounds were obtained from anti-HAA gamma-globulin (3(a)) and zinc insulin taken from pigs (3(b)) and polystyrene latex, using the following coupling components:

I. 0.4 ml of 0.2% bis-diazotized disanisidine
II. 0.4 ml of 0.25% bis-diazotized 4,4'-diamino-diphenylsulfone
III. 0.4 ml of 0.60% diazotized 4-aminophenyl-sulfone-ethoxy-sulfonic acid
IV. 0.8 ml of 0.4% diazotized 2,5-dichloro-4-nitroaniline, dissolved in 10 ml of 0.5-molar ethanolic hydrochloric acid
V. 0.8 ml of 0.2% diazotized aniline
VI. 0.6 ml of 0.2% diazotized naphthylamine and
VII. 0.6 ml of 0.3% bis-diazotized 7-ethoxy-3,9-diamino-acridine in 0.15N aqueous sulfuric acid.

EXAMPLE 4

10 ml of a 40% polystyrene latex suspension disclosed in detail in Example 1 were diluted to 60 ml with 0.2-molar borate buffer containing 2% by volume of glycerol as a stabilizer. The below-mentioned amounts of immunologically active peptides or proteins dissolved in 60 ml of 0.2-molar borate buffer of pH 8.5 were added to this suspension. The suspension was cooled while stirring to 4° C. 0.8 ml of a solution of 2 mg/ml of bis-diazotized benzidine (prepared according to Example 3) was admixed. After stirring had been continued for 1 hour, 7,5 ml of a 20% human albumin solution were added dropwise and the suspension was diluted to 300 ml with 0.2-molar borate buffer of pH 8.5.

The following immunologically active peptides and proteins were used to carry out the process of the invention according to Example 4:

(a) 50 mg of human choriogonadotropin (HCG) having an activity of 3220 U/mg,
(b) 100 mg of rubella virus protein — referred to as hemagglutinin, or the corresponding antibody,
(c) 100 mg of alpha-hemolysin obtained from staphylococci, known as Staphylolysin, or the corresponding antibody.

EXAMPLE 5

3.5 g of lyophilized Trypanosoma of the species *Trypanosoma cruzi*, strain Brasil, the germ of Chagas disease, were suspended in 100 ml of benzene in order to extract lipid (cf. MACKELT Z. Tropenmed. u. Parasit. 11, 152, 1960). After the suspension had been centrifuged for half an hour at 2000 r.p.m. the supernatant solution was eliminated. The residue was dried in a vacuum desiccator, then suspended in 300 ml of physiological sodium chloride solution and treated for 5 minutes by means of ultrasound of 20 k.c./s and of 125 watt. The suspension was then centrifuged for half an hour at 30,000 g. The supernatant substance were combined with ammonium sulfate until 75% of the saturation concentration was reached. The precipitate obtained was isolated by centrifuging for 1 hour at 15,000 g, dissolved in 150 ml of 0.2-molar borate buffer of pH 8.5 and dialyzed against this buffer. This extract served as starting material for the preparation of the Trypanosoma reagent.

10 ml of the 40% polystyrene latex suspension of Example 1 were diluted to 60 ml with 0.2-molar borate buffer containing 2% by volume of glycerol as a stabilizer. 100 mg of Trypanosoma extract dissolved in 100 ml of 0.2-molar borate buffer of pH 8.5 were added to this suspension. The suspension was cooled to 4° C. while stirring. Subsequently, 0.4 ml of a solution of 2 mg/ml of bis-diazotized benzidine (prepared as in Example 3) was admixed. After stirring had been continued for 1 hour, 15 ml of a 20% human albumin solution were added dropwise and the suspension was diluted to 300 ml with 0.2-molar borate buffer of pH 8.5.

EXAMPLE 6

100 mg of dried, fully developed Schistosoma mansoni, the germ of the intestinal and hepatic bilharziasis, obtained in known manner, were suspended in 300 ml of a solution containing 0.5% of sodium chloride, 0.275% of sodium bicarbonate and the sodium salt of p-ethyl-mercuri-thio-benzene-sulfonic acid (registered trade mark Thiocid) in a dilution of 1:5000 (cf. KAGAN and PELLEGRINO Bul. WHO 25, 611, 1961). The suspension was disintegrated, while cooling with ice, by means of a tissue homogenizer at a high speed, left for 1 day at 4° C., diluted to 100 ml with the above-mentioned sodium chloride/sodium bicarbonate solution and centrifuged for 30 minutes at 10,000 g. The supernatant solution was dialyzed against 0.2-molar borate buffer of pH 8.5, whereupon the volume was 120 ml and the protein content was 70 mg.

This extract served as starting material for the preparation of the Schistosoma reagent.

10 ml of the 40% polystyrene latex suspension detailed in Example 1 were diluted to 60 ml with 0.2-molar borate buffer containing 2% by volume of glycerol as a stabilizer. 70 mg of Schistosoma extract, dissolved in 120 ml of 0.2-molar borate buffer of pH 8.5, were added to this suspension. The suspension was cooled to 4° C. while stirring. Then, 0.8 ml of a solution of 2 mg/ml of bis-diazotized benzidine (prepared as in Example 3) was admixed. After stirring had been continued for 1 hour, 11,3 ml of a 20% human albumin solution were added dropwise and the suspension was diluted to 300 ml with 0.2-molar borate buffer of pH 8.5. Instead of the Schistosoma extract hereinbefore described the corresponding antibody obtained from rabbits in known manner can be used in the same way.

EXAMPLE 7

*Entameba histolytica*, the germ of amebic dysentery and, in an advanced stage, of invasive amebiasis (hepatic abscess) was obtained by axenic cultivation according to the process disclosed by L. S. Diamon, J. Parasit. 54, p. 1047-1056 (1968). From the ameba thus cultivated, a protein fraction was obtained by known fractionation methods and prepared into a 3% solution in 0.2-molar sodium borate buffer of pH 8.5. The linkage of 10 ml of this protein fraction to polystyrene latex was performed as disclosed in Example 3, except that 1.2 ml of 0.2% solution of bis-diazotized benzidine were used instead and the mixture was diluted to a volume of 400 ml with a 1% human serum albumin solution in borate buffer of pH 8.5.

EXAMPLE 8

The compound disclosed in Example 3 (a) and obtained from a polystyrene latex suspension and anti-HAA gamma-globulin solution, taken from rabbits, could also be prepared by replacing the polystyrene latex, manufactured by the British Drug Houses Ltd., by latices containing 40% dry material of the following copolymers containing styrene:

(a) A styrene/acrylic acid copolymer dispersion having a ratio of the two components of 100:1.
(b) A styrene/acrylic acid copolymer dispersion having a ratio of the two components of 100:3.
(c) A styrene/methacrylic acid copolymer dispersion having a ratio of the two components of 100:1.
(d) A styrene/methacrylic acid copolymer dispersion having a ratio of the two components of 100:3.

The following examples indicate some uses of the reagents of the invention.

The choriogonadotropin preparation obtained according to the invention (Example 1 *a*) is used for the indication of a pregnancy. By means of antiserum obtained from rabbits by immunization with HCG, HCG is agglutinated in increasing dilutions of the urine of the test subject, and the excess of antibodies against HCG is reacted with the preparation of the invention. If there is an agglutination in all dilutions, the test is negative. If, however, agglutination occurs only in a determined dilution, the test is positive and indicates a pregnancy.

The insulin polystyrene latex compounds (Example 1 *b* and 1 *c*) are used to indicate insulin antibodies in the serum of diabetics to whom insulin has been administered for a prolonged period of time. If there are insulin antibodies, agglutination occurs in a progressive dilution series of the diabetic's serum up to a determined dilution. In higher dilutions, no agglutination occurs. Using insulin-polystyrene latex compounds it is possible to evidence insulin antibodies and even to determine them in a semi-quantitative manner.

The product obtained according to the invention using antiimmunoglobulin M (anti-IgM) from rabbits (Example 1 *d*) is used as a reagent for indicating an increased IgM-concentration in the serum of new-born. IgM is generally not formed by the fetus nor passes from the material to the fetal blood circulation system. It can, therefore, not be evidenced in the serum of new-born. If, however, the fetus has suffered from an intra-uterinal disease, for example from German measles or toxoplasmosis, the fetus produces IgM, and a relatively high IgM concentration is determined in the serum of new-born using the anti-IgM reagent of the invention. Hence the reagent is suitable as a basis for assuming that the new-born have been suffering from an intra-uterinal disease.

The preparation obtained according to the invention using anti-HAA gamma-globulin from rabbits (Example 1 *e*) is used to indicate HAA in the serum of blood donors and for the diagnosis of serum hepatitis where HAA shows already in the prodromal stage. In a serum sample taken from a person who has been suffering from serum heptatitis, agglutination of the suspension prepared according to the invention occurs. In contradistinction thereto, the suspension remains unaltered if a serum sample free from hepatitis antigen is tested.

The rubella virus diagnostic agent prepared according to the invention (Example 4 b) serves for indicating rubella antibodies in the serum, especially of women capable of bearing children, since an infection with German measles during pregnancy may damage the fetus, referred to as virus embryopathy and marked as a beginning of congenital deformites. If the serum is taken from a woman who has suffered from German measles or has been vaccinated with German measles vaccine, the German measles diagnostic agent, prepared according to the invention and added to the serum, agglutinates, If, however, the test is negative, an immunization with German measles vaccine is indicated.

The product of the invention containing alpha-hemolysin, a metabolism product of staphylococci, as an immunologically active protein (Example 4 c) serves for the diagnosis of rheumatic diseases. It forms an agglutination with the anti-alpha-hemolysin contained in the rheumatic's serum. Healthy people's values are between 2 and 4 units, pathological values are higher. The test is as sensitive as to indicate even 1 to 2 units of anti-alpha-hemolysin. The product of the invention can be standardized with the standard serum of the National Serum Institute at Copenhagen.

The Trypanosoma reagent obtained according to Example 5 shows an agglutination with the serum of patients who suffer from Chagas disease. There is no reaction if serum of healthy people is used.

The Schistosoma reagent prepared according to Example 6 shows an agglutination with sera of patients who suffered from bilharziasis. There is no reaction if serum of healthy people is used.

Further possibilities of application are the following:

1. Latex-IgE reagent
    As a diagnostic agent for the evidence of increased IgE-concentration in the serum, in the case of allergy and parasitological diseases.
2. Latex-IgA reagent
    As a diagnostic agent for the screening of new-born and for the evidence of increased IgA-concentration in the serum of new-born, as it may, for example, occur after intra-uterinal infections.
3. Latex-alpha$_1$-fetoprotein reagent
    As a diagnostic agent for the evidence of alpha$_1$-fetoprotein in the serum, as it may occur in the case of primary liver carcinoma, rarely of teratoblastoma.
4. Latex-PP$_1$ reagent
    As a diagnostic agent for the evidence of pregnancy-specific protein PP$_1$ in the serum and the urine; for the diagnosis of pregnancy and the control of the course of pregnancy.
5. Latex-ameba reagent
    As a diagnostic agent for the evidence of antibodies against amebas and as an auxiliary diagnostic agent in the case of amebic infections (diagnosis of invasive amebiasis).
6. Latex-HPL reagent
    As a diagnostic agent for the evidence of human placenta lactogen in the serum of pregnant women and for the control of the course of pregnancy.
7. Latex-fibrinogen-split product D and latex-fibronogen-split product E
    As diagnostic agents for the evidence of fibrinogen splits D and E in the serum and in the case of all forms of hyper-fibrinolysis (e.g., coagulopathy due to expenditure; thrombolytical therapy) and for the evidence of fibrinopeptiduria in the case of transplantation of kidneys, nephritis and nephroses.
8. Latex-myoglobin reagent
    As a diagnostic agent for the evidence of myoglobin in the serum and urine, for example in the early diagnosis of cardiac infarction.
9. Latex-haptoglobin reagent
    For the evidence of haptoglobin insufficiency which may lead to transfusion troubles, if hemolysis occurs.

What we claim is:

1. In a process for chemically bonding a protein or peptide to a polymeric carrier which is a styrene homopolymer or a copolymer of styrene with less than 50 percent by weight of acrylic acid or methacrylic acid by contacting (1) a homogeneous aqueous latex suspension of said polymeric carrier, (2) said protein or peptide, and (3) an aromatic diazonium compound at a weakly alkaline pH, the improvements which comprise contacting (1), (2) and (3) at a temperature below room temperature and subsequently adding albumin to the mixture to give an albumin concentration between 0.5 and 1.5 percent in the mixture.

2. A method as in claim 1, wherein said latex and diazonium compound are first combined and said protein or peptide is then combined therewith.

3. A method as in claim 1, wherein said latex and protein or peptide are first combined and said diazonium compound is then combined therewith.

4. A method in claim 1, wherein said diazonium compound is a diazotized amine selected from the group consisting of 2-naphthylamine; 7-ethoxy-3,9-diaminoacridine; aniline; substituted anilines; phenylene diamine, benzidine; dianisidine; diamino-diphenylmethane; diamino-diphenyl-sulfone; benzidine sulfonic acids and p-amino-phenylsulfone-ethoxy-sulfonic acids.

5. A method as in claim 1, wherein said protein or peptide is a plasmaprotein; a proteohormone; or a viral, bacterial, protozoic, or helminthic protein.

6. A method as in claim 1, wherein said protein or peptide is an IgE-globulin or the corresponding antibody.

7. A method as in claim 1, wherein said protein or peptide is the antibody corresponding to haptoglobin.

8. A method as in claim 1, wherein said protein or peptide is the antibody corresponding to α1-antitrypsin.

9. A method as in claim 1, wherein said protein or peptide is PP$_1$,PP$_2$, or PP$_3$ pregnancy proteins, or the antibody corresponding to PP$_1$, PP$_2$ or PP$_3$.

10. A method as in claim 1, wherein said protein or peptide is the antibody corresponding to transaminase.

11. A method as in claim 1, wherein said protein or peptide is a rubella virus protein or the corresponding antibody.

12. A method as in claim 1, wherein said protein or peptide is a staphylolysin.

13. A method as in claim 1, wherein said protein or peptide is a bilharziasis antigen or the corresponding antibody.

14. A method as in claim 13, wherein said bilharziasis antigen or the antibody is derived from Schistosoma mansoni.

15. A method as in claim 1 wherein said protein or peptide is a protein fraction derived from *Entameba histolytica*.

16. A polymeric carrier having a protein or peptide bonded thereto, prepared by the method of claim 1.

17. A polymeric carrier having a protein or peptide bonded thereto, prepared by the method of claim 7.

18. A polymeric carrier having a protein or peptide bonded thereto, prepared by the method of claim 8.

19. A polymeric carrier having a protein or peptide bonded thereto, prepared by the method of claim 11, wherein said protein or peptide is a rubella virus protein.

20. A polymeric carrier having a protein or peptide bonded thereto, prepared by the method of claim 12.

21. A polymeric carrier having a protein or peptide bonded thereto, prepared by the method of claim 13, wherein said protein or peptide is a bilharziasis antigen.

22. A polymeric carrier having a protein or a peptide bonded thereto, prepared by the method of claim 15.

* * * * *

UNITED STATES PATENT AND TRADEMARK OFFICE
CERTIFICATE OF CORRECTION

PATENT NO. : 4,118,349
DATED : October 3, 1978
INVENTOR(S) : Bonacker et al.

It is certified that error appears in the above-identified patent and that said Letters Patent are hereby corrected as shown below:

In the Heading, Item [30], after "Fed. Rep. of Germany" change the number "212348" to --2123489--.

Signed and Sealed this

Nineteenth Day of December 1978

[SEAL]

Attest:

RUTH C. MASON
Attesting Officer

DONALD W. BANNER
Commissioner of Patents and Trademarks